(12) United States Patent
Schlosberg et al.

(10) Patent No.: US 7,504,527 B2
(45) Date of Patent: *Mar. 17, 2009

(54) LOW CORROSIVE INTEGRATED PROCESS FOR PREPARING DIALKYL CARBONATES

(75) Inventors: Richard H. Schlosberg, Bridgewater, NJ (US); J. Scott Buchanan, Lambertville, NJ (US); Jose Guadalupe Santiesteban, Bethlehem, PA (US); Zhaozhong Jiang, Edison, NJ (US); William A. Weber, Burlington, NJ (US)

(73) Assignee: Badger Licensing, LLC, Cambridge, MA (US)

( * ) Notice: Subject to any disclaimer, the term of this patent is extended or adjusted under 35 U.S.C. 154(b) by 398 days.

This patent is subject to a terminal disclaimer.

(21) Appl. No.: 10/641,596

(22) Filed: Aug. 15, 2003

(65) Prior Publication Data

US 2004/0054214 A1  Mar. 18, 2004

Related U.S. Application Data

(60) Division of application No. 10/105,550, filed on Mar. 25, 2002, now Pat. No. 6,774,256, which is a continuation-in-part of application No. 09/887,642, filed on Jun. 22, 2001, now Pat. No. 7,084,292.

(51) Int. Cl.
*C07C 69/96* (2006.01)
(52) U.S. Cl. ................................ 558/277
(58) Field of Classification Search ............ 558/277
See application file for complete search history.

(56) References Cited

U.S. PATENT DOCUMENTS

| | | | | |
|---|---|---|---|---|
| 2,873,282 | A | 2/1959 | McClellan | 260/340.2 |
| 3,535,341 | A | 10/1970 | Frevel et al. | 260/340.2 |
| 3,642,858 | A | 2/1972 | Frevel et al. | 260/463 |
| 4,434,105 | A | 2/1984 | Buysch et al. | 260/463 |
| 4,691,041 | A | 9/1987 | Duranleau et al. | 558/277 |
| 5,218,135 | A | 6/1993 | Buysch et al. | 558/277 |
| 5,489,703 | A * | 2/1996 | Pacheco et al. | 558/277 |
| 5,498,743 | A | 3/1996 | Shih et al. | 558/277 |
| 5,498,744 | A | 3/1996 | Jentsch et al. | 558/277 |
| 6,010,976 | A | 1/2000 | Ryu | 502/156 |
| 6,207,850 | B1 | 3/2001 | Santiesteban et al. | |
| 6,342,623 | B1 | 1/2002 | Hoglen et al. | |
| 6,407,279 | B1 | 6/2002 | Buchanan et al. | 558/277 |
| 6,774,256 | B2 * | 8/2004 | Schlosberg et al. | 558/277 |
| 2003/0023109 | A1 | 1/2003 | Schlosberg et al. | 558/277 |

FOREIGN PATENT DOCUMENTS

| | | |
|---|---|---|
| DE | 4 326 906 | 2/1995 |
| EP | 0 119 840 | 9/1984 |
| EP | 0 460 732 | 12/1991 |
| EP | 0 478 073 | 4/1992 |
| EP | 0 534 545 | 3/1993 |
| EP | 1 125 915 | 8/2001 |
| GB | 2 107 712 | 5/1983 |
| WO | WO 00/73256 | 12/2000 |
| WO | WO 02/070452 | 9/2002 |
| WO | WO 03/000641 | 1/2003 |

OTHER PUBLICATIONS

DE 4 326 906—Abstract of Patent (published Feb. 16, 1995).
Bhamage B.M., et al: "Synthesis of dimethyl carbonate and glycols from carbon dioxide, epoxides, and methanol using heterogeneous basic metal oxide catalysts with high activity and selectivity", Applied Catalysis A: General, Elsevier Science, Amsterdam, NL, vol. 219, No. 1-2, pp. 259-266 (Oct. 5, 2001).
Chem Systems, "Developments in Dimethyl Carbonate Production Technologies," 99/00S6, pp. 1-73 (May 2000).
Chem Systems, "Dimethyl Carbonate via Ethylene Carbonate," 90S7, pp. 1-36, (Dec. 1991).
Hong Zhu et al: "Synthesis of Propylene Carbonate and Some Dialkyl Carbonates in the Presence of Bifunctional Catalyst Compositions", Polymers for Advanced Technologies, John Wiley & Sons, Chichester, GB, vol. 7, No. 8, pp. 701-703 (Aug. 1, 1996).
John J. McKetta et al., "Ethanol as Fuel: Options, Advantages, and Disadvantages to Exhaust Stacks, Cost," Encyclopedia of Chemical Processing and Design, New York, vol. 20, pp. 237-243, (1984).
J.J. McKetta et al., "Ethylene Carbonate and Propylene Carbonate," Encyclopedia of Chemical Processing and Design, New York, pp. 177-201 (1984).

(Continued)

*Primary Examiner*—Laura L. Stockton
(74) *Attorney, Agent, or Firm*—Peter W. Roberts; Roberts, Mlotkowski, Safran & Cole PC

(57) ABSTRACT

An integrated process for the production of a dialkyl carbonate and a diol from an alkylene oxide, carbon dioxide and an aliphatic monohydric alcohol is described in which an alkylene oxide is first reacted with carbon dioxide in the presence of a halogen-free carbonation catalyst to provide a corresponding cyclic carbonate and the cyclic carbonate is then reacted with an aliphatic monohydric alcohol in the presence of the carbonation catalyst and/or a transesterification catalyst and recycling the carbonation catalyst to provide a corresponding dialkyl carbonate and diol, wherein the dialkyl carbonate product exhibits a halogen concentration of about 5 ppm or less.

1 Claim, 4 Drawing Sheets

OTHER PUBLICATIONS

Shao-Hwa Wang, "The Coproduction of Dimethyl Carbonate and Ethylene Glycol by Transesterification," Process Economics Program, PEP Review No. 92-1-1, pp. 1-30, (May 1993).

W.J. Peppel, "Preparation and Properties of the Alkylene Carbonates," Jefferson Chemical Co., vol. 50, No. 5, pp. 767-770 (May 1958).

Watanabe Y., et al: "Hydrotalcite-type Materials as Catalysts for the Synthesis of Dimethyl Carbonate from Ethylene Carbonate and Methanol", Microporous and Mesoporous Materials, Elsevier Science Publishing, New York, vol. 22, No. 1-3, pp. 399-407 (Jun. 17, 1998).

* cited by examiner

LOW CORROSIVE INTEGRATED PROCESS FOR PREPARING DIALKYL CARBONATES

The present application is a divisional of, and claims the effective filing date of U.S. application Ser. No. 10/105,550, filed Mar. 25, 2002, now U.S. Pat. No. 6,774,256, which is a continuation-in-part of U.S. patent application, Ser. No. 09/887,642, filed Jun. 22, 2001, now U.S. Pat. No. 7,084,292.

This invention relates to a low corrosive process for preparing dialkyl carbonates and diols. More specifically, the present invention relates to an integrated process for preparing dialkyl carbonates and diols from alkylene oxides, carbon dioxide and alcohols having a chlorine concentration of 5 ppm or less, preferably 2 ppm or less.

BACKGROUND OF THE INVENTION

Dialkyl carbonates are important intermediates for the synthesis of fine chemicals, pharmaceuticals and plastics and are useful as synthetic lubricants, solvents, plasticizers and monomers for organic glass and various polymers, including polycarbonate, a polymer known for its wide range of uses based upon its characteristics of transparency, shock resistance and processability.

Industrially, dimethyl carbonate (DMC) is used in the production of polycarbonates and has the potential to be used as an environmentally friendly fluid for numerous solvent-related applications and conceivably even as a fuel oxygenate (e.g., methyl tertiary butyl ether replacement).

Historically, DMC was prepared from the highly toxic intermediate phosgene, COCl2. Currently, it is prepared via oxidative carbonylation of methanol using a copper(I) chloride catalyst together with a halogen mitigation step using HCl. This method is based on copper(I) chloride as the catalyst and demonstrated in EP 534,545 B1 and EP 460,732 A1. The overall copper catalyzed reaction is shown in equation (1) below:

$$CO + 2CH_3OH + 1/2O_2 \rightarrow (CH_3O)_2CO + H_2O \qquad (1)$$

The copper(I) chloride catalyst is very insoluble in this system and, thus, is a limiting component in the catalytic cycle. Hydrochloric acid is also added as a component in this oxidative carbonylation system during a mitigation step. This was done to prevent the oxidation of Cu(I) to Cu(II) in the presence of oxygen and water since Cu(I) is believed to be the active species in this system. This copper chloride catalyst-based oxidative carbonylation system, which is run between 120° C. and 160° C., is extremely corrosive and requires costly components (e.g., glass lined reactors). Failure in the glass lining could lead to rupture or explosion. Two other notable processes for the production of DMC are disclosed in U.S. Pat. Nos. 6,010,976 and 5,498,744. U.S. Pat. No. 6,010,976 discloses a catalytic reaction of urea with methanol to first form the carbamate, which is further reacted to form DMC, ammonia and carbon dioxide. U.S. Pat. No. 5,498,744 discloses a process that reacts methylnitrite with carbon monoxide over a catalyst to form DMC and (NO)x which is toxic.

DMC, due to its low toxicity and low atmospheric reactivity, has tremendous growth potential as a possible replacement for methyl tertiary butyl ether (MTBE), as a fluorocarbon solvent replacement in the electronics industry and as an environmentally friendly solvent for use in the production of polycarbonates. The problems with MTBE and fluorocarbons, and phosgene are widely publicized. The growth of DMC use has been, in part, limited by the difficulties in commercial production. An efficient and environmentally friendly method for the large-scale production of DMC would be highly desirable, especially a process that eliminates the need for a chloride-based catalyst and hydrochloric acid mitigation, which causes corrosion of the reaction vessel and impurities in the resultant product.

Accordingly, Applicants have developed an improved low corrosive process for the production of alkyl carbonates, and, in particular, DMC, starting from carbon monoxide, oxygen and alcohol in the presence of a triesterification catalyst, wherein the halogen (e.g., chlorine) concentration of the alkyl carbonate product is 5 ppm or less.

SUMMARY OF THE INVENTION

According to the present invention, it has now been found that a dialkyl carbonate and a diol, and more specifically dimethyl carbonate and ethylene glycol, can be prepared according to an integrated process having high productivity which uses a halogen-free carbonation catalyst, by:

reacting an alkylene oxide (ethylene oxide in the case of dimethyl carbonate and ethylene glycol) with carbon dioxide in the presence of a halogen-free carbonation catalyst in a first reaction zone at a temperature in the range of about 50° C. to 250° C. and at a pressure of at least about 200 psi to provide a crude cyclic carbonate stream containing a cyclic carbonate (e.g., ethylene carbonate in the case of dimethyl carbonate and ethylene glycol) and the carbonation catalyst; and reacting the cyclic carbonate (e.g., ethylene carbonate) from the crude cyclic carbonate stream with an aliphatic monohydric alcohol (e.g., methanol in the case of dimethyl carbonate and ethylene glycol), in the second reaction zone in the presence of the carbonation catalyst in the crude cyclic carbonate stream to provide a crude product stream containing a dialkyl carbonate (e.g., dimethyl carbonate) and diol (e.g., ethylene glycol). The crude product stream preferably having a halogen concentration of about 5 ppm or less, more preferably about 2 ppm or less.

In another aspect of the present invention, it has now been found that a dialkyl carbonate and a diol, and more specifically dimethyl carbonate and ethylene glycol, can be prepared according to an integrated process having high productivity by using both a halogen-free carbonation catalyst and a transesterification catalyst, by:

reacting an alkylene oxide (ethylene oxide in the case of dimethyl carbonate and ethylene glycol) with carbon dioxide in the presence of a halogen-free carbonation catalyst in a first reaction zone to provide a crude cyclic carbonate stream containing cyclic carbonate (ethylene carbonate in the case of dimethyl carbonate and ethylene glycol) and the carbonation catalyst; and reacting at least a portion of the cyclic carbonate (e.g., ethylene carbonate) from the crude cyclic carbonate stream with an aliphatic monohydric alcohol (methanol in the case of dimethyl carbonate and ethylene glycol), in a second reaction zone in the presence of a transesterification catalyst to provide a crude product stream containing a dialkyl carbonate (e.g., dimethyl carbonate) and diol (e.g., ethylene glycol). The crude product stream preferably having a halogen concentration of about 5 ppm or less, more preferably about 2 ppm or less.

Additional objects, advantages and novel features of the invention will be set forth in part in the description and examples which follow, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE PREFERRED EMBODIMENT

Figure 1:
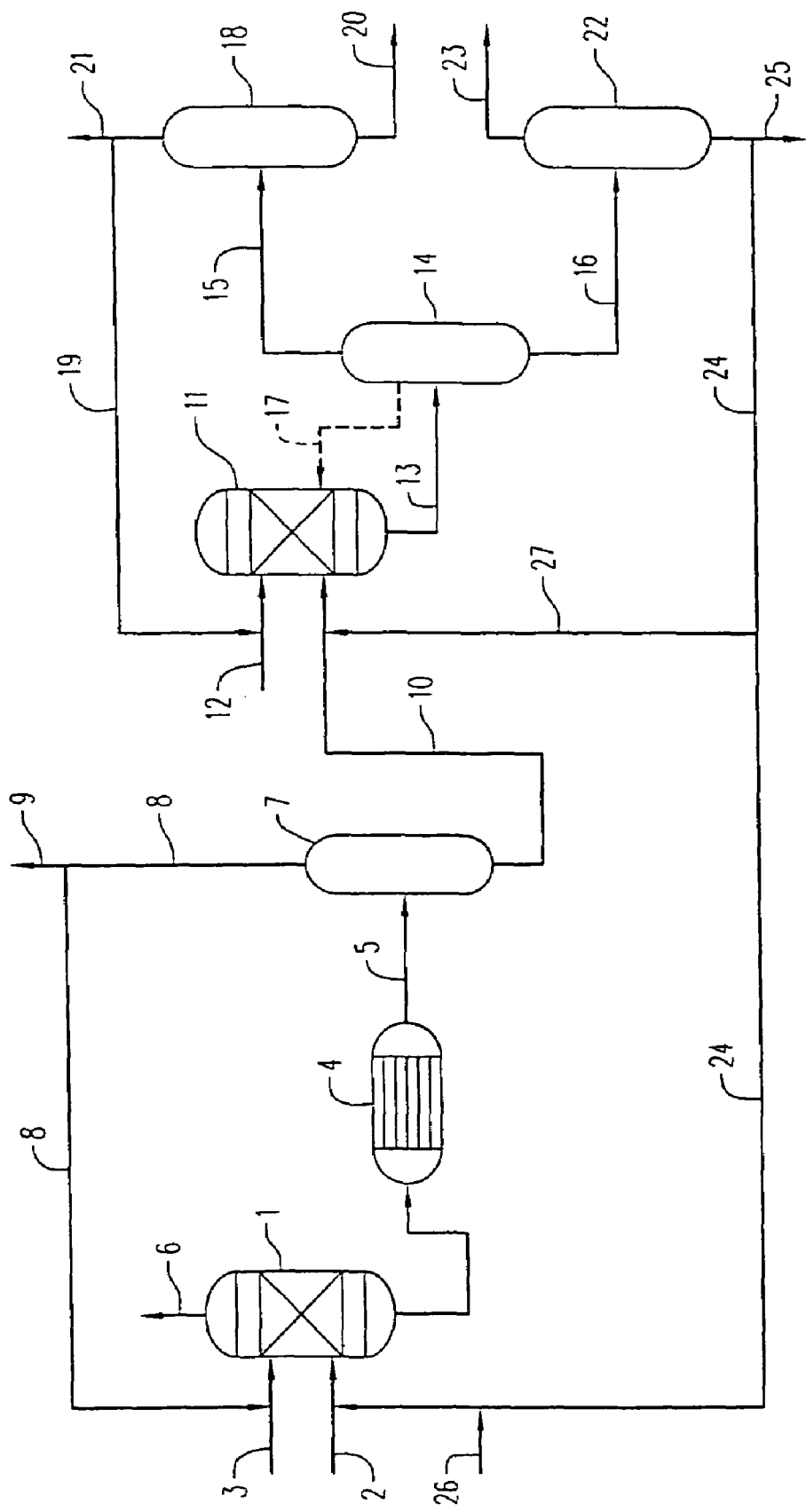
FIG. 1 is a schematic of a preferred embodiment of the integrated process, which utilizes a circulating halogen-free carbonation catalyst.

The present invention is a continuous integrated process for preparing low corrosive dialkyl carbonates and diols from alkylene oxides, carbon dioxide and aliphatic monohydric alcohols, wherein the resultant dialkyl carbonates and diols exhibit a halogen (i.e., chlorine) concentration of about 5 ppm or less, more preferably about 2 ppm or less.

In preparing the dialkyl carbonates and diols, an alkylene oxide is first reacted with CO2 in the presence of a halogen-free carbonation catalyst (e.g., [1,1'(1-butylbenzimidazol-2yl)pentane]copper(II) di(trifluoromethanesulfonate), or hydroxides, carbonates or bicarbonates of quaternary ammonium bases) to provide a corresponding cyclic carbonate. Preferably, the alkylene oxide is represented by structural formula set forth below in equation (I). Examples of such alkylene oxides include ethylene oxide, propylene oxide, styrene oxide, trimethylene oxide, cyclohexene oxide, and the like. Of these alkylene oxides, ethylene oxide and propylene oxide are preferably used because of their good availability and high demand end products. Ethylene oxide is most preferably used. The alkylene oxide feed may contain various impurities, especially the impurities resulting from its manufacture. For instance, ethylene oxide which is made by selective oxidation of ethylene may contain carbon dioxide, water and aldehydes.

Preferred cataysts are the quaternary ammonium compounds having the following structural formula:

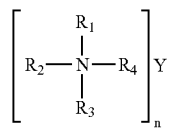

in which $R_1$, $R_2$, $R_3$ and $R_4$ are the same or different, are alkyl, aralkyl, alkenyl (a monovalent radical containing a double bond including, for example, allyl and vinyl) or aminoalkyl groups containing from 1 to 20 carbon atoms, the sum of the carbon atoms $R_1$, $R_2$, $R_3$ and $R_4$ is not less than 4 and not more than 40, Y is a hydroxide carbonate or bicarbonate radical and the value of n is equal to the valence of Y, and quaternary ammonium compounds having the following structural formula:

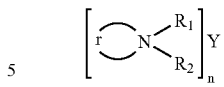

in which $R_1$, $R_2$, n and Y have the meaning noted above and r is a divalent radical as follows:

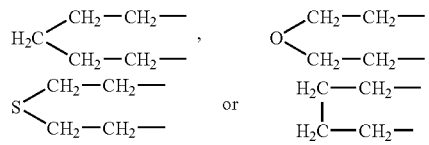

Examples of quaternary ammonium compounds suitable as catalysts in accordance with this invention and having a structural formula corresponding to the first formula above given are trimethyl benzyl ammonium hydroxide, tetraethyl ammonium hydroxide, trimethyl cetyl ammonium hydroxide, trimethyl butyl ammonium hydroxide, tetrabutyl ammonium hydroxide, diethyl diamyl ammonium hydroxide, other tetraalkyl ammonium hydroxides in which the alkyl groups are the same or different and each alkyl group contains from 1 to 20 carbon atoms, and the corresponding carbonates and bicarbonates of the above enumerated compounds.

Examples of quaternary ammonium compounds having a structural formula corresponding to the second formula above given are methyl ethyl piperidinium hydroxide, methyl decyl piperidinium hydroxide, 4,4-benzyl methyl morpholinium hydroxide, 4,4-dially morpholinium hydroxide, 4,4-methyl hexyl morpholinium hydroxide, 4,4-ethyl butyl morpholinium hydroxide, 4,4-diethyl thiomorpholinium hydroxide, other dialkyl piperidinium, pyrrolidinium, morpholinium, and thiomorpholinium compounds.

N,N,N,N',N',N'-hexamethyl-ethylene-bis-ammonium hydroxide, carbonate and bicarbonate are also effective catalysts. The formula for the hydroxide is:

$(H_3C)_3N-CH_2-CH_2-N-(CH_3)_3(OH)_2$

The quaternary ammonium compound may be obtained as such from any available source or produced in any desired manner as set forth in U.S. Pat. No. 2,873,282, which is incorporated herein by reference.

The first carbonation reaction involving this preferred alkylene oxide may be represented by the following:

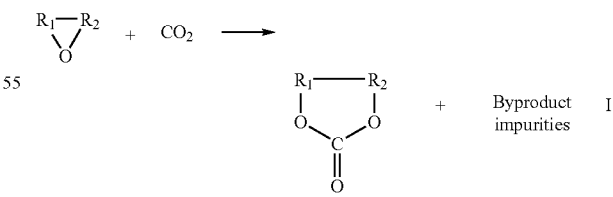

wherein $R_1$ and $R_2$ independently of one another denote a divalent group represented by the formula $-(CH_2)_m-$, wherein m is an integer from 1 to 3, which is unsubstituted or substituted with at least one substituent selected from the group consisting of $C_1$-$C_{10}$ alkyl group and a $C_6$-$C_{10}$ aryl group, wherein $R_1$ and $R_2$ can share the same substituent.

The carbon dioxide to be employed can contain inert gases, such as nitrogen, hydrogen, carbon monoxide and lower hydrocarbons, and can originate from natural sources or industrial gases or waste gases. The water content of the carbon dioxide is preferably below 1 mol %, and the concentration of sulfur is preferably below 100 ppm by weight.

The content and amount of carbon dioxide will depend on the reaction rate, reactor type and specific catalyst used, and is adjusted to maximize the economics of the process. Preferably, the molar ratio of alkylene oxide to carbon dioxide is about 1:1, but an excess of carbon dioxide is also contemplated. Therefore, according to the present invention, the molar ratio of alkylene oxide to carbon dioxide is preferably in the range from about 1:0.9 to 1:15 and more preferably in the range from about 1:1 to 1:3.

In one aspect of the present invention a halogen-free carbonation catalyst is used in both reaction zones of the process. In the first reaction zone of the first aspect, the reactants (i.e., alkylene oxide and carbon dioxide) are contacted in the presence of the halogen-free carbonation catalyst.

The catalyst can be introduced to the reactor as part of a recycle stream, the fresh feed, make-up or a combination of these. The amount of catalyst measured as the concentration of catalyst in the reactor effluent is generally about 0.05 to 5% by weight, preferably about 0.15 to 2.0% by weight.

In the first aspect, the carbonation reaction is preferably carried out in a continuous mode utilizing various reaction configurations, such as a stirred-tank, tubular, fixed or packed-bed reactor, in a single or multiple-reactor configuration, at from about 50° C. up to about 250° C., preferably between about 100° C. up to about 200° C. and more preferably between about 150° C. up to about 200° C., and at pressures ranging from about at least 1379 kPa (200 psi) up to about 13790 kPa (2000 psi), preferably from about 2069 kPa (300 psi) up to about 8964 kPa (1300 psi) and more preferably from about 3448 kPa (500 psi) up to about 6895 kPa (1000 psi). In the preferred mode of operation, the reactor temperature and pressure are optimized to ensure a relatively high conversion and selectivity to the desired alkylene carbonate. A provision for heat removal from the reactor is normally required, since the carbonation reaction is exothermic.

Preferably, the effluent from the carbonation reaction zone is fed into a second carbonation reaction zone that can operate under different conditions or a different configuration to provide a greater overall conversion of the alkylene oxide, preferably greater than 90% overall conversion. Preferably, the second carbonation reaction zone is a separate tubular polishing reactor which operates at from about 50° C. up to about 250° C., preferably between about 100° C. up to about 200° C. and at pressures ranging from at least about 1379 kPa (200 psi) up to about 13790 kPa (2000 psi), preferably from about 2069 kPa (300 psi) to about 8964 kPa (1300 psi).

Typically, impurities are formed in the carbonation reaction in the form of by-products. Glycols may be formed along with the alkylene carbonates, especially if there is water present in the system. For example, by reacting ethylene oxide with CO2 to produce ethylene carbonate, typically ethylene glycol and some higher molecular weight glycols are produced.

The carbonation reactor effluent, either from the first carbonation reaction zone or from the second carbonation reaction zone (if used), is preferably subjected to a flash separation to remove the volatiles, such as unreacted CO2 and alkylene oxide.

The effluent from the carbonation reaction is preferably not subjected to any further separation. Thus, the cyclic carbonate and the by-product impurities produced in the carbonation reaction, along with the homogeneous catalyst, are then fed to the transesterification reactor, where the cyclic carbonate is reacted with an aliphatic monohydric alcohol in the presence of the homogeneous carbonation catalyst to provide a corresponding dialkyl carbonate and diol.

Preferably, the aliphatic monohydric alcohol has a boiling point lower than that of the produced diol. The type of an aliphatic monohydric alcohol which can be used in the present invention varies depending on the particular cyclic carbonate produced by the carbonation reaction. Examples of such aliphatic monohydric alcohols include methanol, ethanol, n-propanol, iso-propanol, alkyl alcohol, butanol (including isomers of butanol), 3-butene-1-ol, amyl alcohol (isomers), hexyl alcohol (isomers), heptyl alcohol (isomers), octyl alcohol (isomers), nonyl alcohol (isomers), decyl alcohol (isomers), undecyl alcohol (isomers), dodecyl alcohol (isomers), cyclopentanol, cyclohexanol, cycloheptanol, cyclooctanol, methylcyclopentanol (isomers), ethylcyclopentanol (isomers), methylcyclohexanol (isomers), ethylcyclohexanol (isomers), dimethylcyclohexanol (isomers), diethylcyclohexanol (isomers), phenylcyclohexanol (isomers), benzyl alcohol, phenethyl alcohol (isomers), phenylpropanol (isomers), and the like. The above mentioned aliphatic monohydric alcohol may be substituted with at least one substituent, such as a halogen atom, a lower alkoxy group, a cyano group, an alkoxycarbonyl group, an aryloxycarbonyl group, an acyloxy group, a nitro group or the like.

Of the aliphatic monohydric alcohols, an alcohol having 1 to 6 carbon atoms is preferably used. When ethylene carbonate is the cyclic carbonate, an alcohol having 1 to 4 carbon atoms, i.e., methanol, ethanol, propanol (isomers) or butanol (isomers) is preferably used. The method of the present invention can be employed advantageously especially when methanol and ethylene carbonate are used as feedstocks for the transesterification reaction.

According to the present invention, it has now been found that it is unnecessary to purify the cyclic carbonate or separate the carbonation catalyst to achieve relatively high yields and selectivity to the desired dialkyl carbonate and diol, resulting in significant economic benefits and advantage due to the elimination of the separation and purification steps, e.g., one or more evaporators and two vacuum distillation columns, previously thought necessary. In addition to lower operating and capital costs associated with eliminating these steps, a yield benefit is realized by eliminating losses of cyclic carbonate attributable to the separation and purification steps.

As such, an integrated process is provided which produces both a dialkyl carbonate and a diol with high productivity. In accordance with the present invention, the term "productivity" means the yield per unit volume of both the carbonation and transesterification zones per unit time, i.e., the space time yield for the overall integrated process.

This transesterification reaction may be represented by the following:

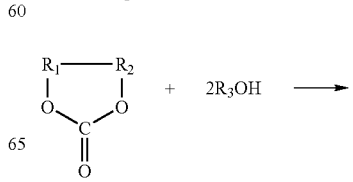

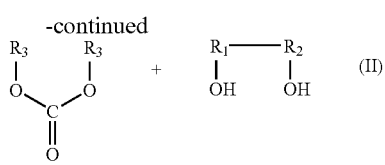

(II)

wherein $R_1$ and $R_2$ independently of one another denote a divalent group represented by the formula —$(CH_2)_m$—, wherein m is an integer from 1 to 3, which is unsubstituted or substituted with at least one substituent selected from the group consisting of $C_1$-$C_{10}$ alkyl group and a $C_6$-$C_{10}$ aryl group, wherein $R_1$ and $R_2$ can share the same substituent; and $R_3$ is a monovalent aliphatic $C_1$-$C_{12}$ hydrocarbon group which is unsubstituted or substituted with at least one substituent selected from the group consisting of a $C_1$-$C_{10}$ alkyl group and a $C_6$-$C_{10}$ aryl group. Other components in the feed to the transesterification reactor may include various other species, commonly hydroxyalkyl carbonates and dialkyl carbonates, as fresh feed or in one or more recycle streams.

The reactants to the transesterification reaction (i.e., the cyclic carbonate and the aliphatic monohydric alcohol) are contacted in the presence of the carbonation catalyst from the carbonation reaction. The transesterification reaction is preferably carried out in a continuous mode utilizing various reactor configurations, such as, stirred-tank or tubular reactors, in a single or multiple-reactor configuration, or a reactive distillation column, at from about 50° C. up to about 250° C., preferably between about 75° C. up to about 170° C., and at pressures ranging from about atmospheric pressure up to about 13790 kPa (2000 psi), preferably from about 138 kPa (20 psi) up to about 2069 kPa (300 psi). In the preferred mode of operation, the reactor temperature and pressure are optimized to ensure a relatively high conversion and selectivity to the desired dialkyl carbonate and diol and to optimize the economics of the overall integrated process. Generally, a reactive distillation column will tend to give higher conversions of ethylene carbonate and methanol.

In the second aspect of the present invention a halogen-free carbonation catalyst is used in the first carbonation reaction zone and a heterogeneous transesterification catalyst is used in the second transesterification reaction zone. This aspect is similar to the first aspect except for the following process conditions which are preferred for the two catalyst process of the second aspect of the present invention.

In the second aspect, the reactants (i.e., alkylene oxide and carbon dioxide) are contacted in the presence of a carbonation catalyst. In the second aspect of the present invention (i.e., the carbonation-transesterification catalyst process) the carbonation catalyst is preferably [1,1'(1-butylbenzimidazol-2yl)pentane]copper(II) di(trifluoromethanesulfonate), or hydroxides, carbonates or bicarbonates of quaternary ammonium bases.

The halogen-free carbonation catalyst can be introduced to the reactor as part of a recycle stream, the fresh feed, make-up or a combination of these. The amount of catalyst measured as the concentration of catalyst in the reactor effluent is generally about 0.05 to 5% by weight, preferably about 0.15 to 2.0% by weight.

In the second aspect, the carbonation reaction is preferably carried out in a continuous mode utilizing various reaction configurations, such as a stirred-tank, tubular, fixed or packed-bed reactor, in a single or multiple-reactor configuration, at from about 50° C. up to about 250° C., preferably between about 100° C. up to about 200° C., and at pressures ranging from about atmospheric pressure up to about 13790 kPa (2000 psi), preferably from about 2069 kPa (300 psi) up to about 8964 kPa (1300 psi). In the preferred mode of operation, the reactor temperature and pressure are optimized to ensure a relatively high conversion and selectivity to the desired alkylene carbonate. A provision for heat removal from the reactor is normally required, since the carbonation reaction is exothermic.

Preferably, the effluent from the carbonation reaction zone of the second aspect is fed into a second carbonation reaction zone that can operate under different conditions or a different configuration to provide a greater overall conversion of the alkylene oxide, preferably greater than 90% overall conversion. Preferably, the second carbonation reaction zone is a separate tubular polishing reactor which operates at from about 50° C. up to about 250° C., preferably between about 100° C. up to about 200° C. and at pressures ranging from about atmospheric pressure up to about 13790 kPa (2000 psi), preferably from about 2069 kPa (300 psi) to about 8964 kPa (1300 psi).

According to the second aspect of the present invention, it has now been found that it is unnecessary to purify the cyclic carbonate or separate the halogen-free carbonation catalyst to achieve relatively high yields and selectivity to the desired dialkyl carbonate and diol, resulting in significant economic benefits and advantage due to the elimination of the purification steps, e.g., one or more evaporators and two vacuum distillation columns, previously thought necessary. In addition to lower operating and capital costs associated with eliminating the purification steps, a yield benefit is realized by eliminating losses of cyclic carbonate attributable to the purification steps.

In the second aspect, the reactants to the transesterification reaction (i.e., the cyclic carbonate and the aliphatic monohydric alcohol) are contacted in the presence of a heterogeneous transesterification catalyst. The transesterification catalyst can typically include any heterogeneous catalyst known in the art which provides adequate reaction kinetics in the presence of the carbonation catalyst and minimizes side reactions with the impurities contained in the cyclic carbonate. Examples of such catalysts include ion-exchangers, such as, anion-exchange resins having tertiary amino groups, amide groups, or at least one type of ion-exchange group selected from the group consisting of sulfonate, carboxylate and phosphate groups; strongly basic solid anion-exchangers having quaternary ammonium groups as ion-exchange groups and the like; inorganic metal oxides; solid inorganic compounds, such as, silica, alumina, magnesia and transitional aluminas, such as, pseudoboehmite, silica-alumina, silica-magnesia, aluminosilicate, gallium silicate, various types of zeolites, various types of metal-exchanged zeolites, ammonium-exchanged zeolites, inorganic solid support catalysts containing metals, and the like. The term "transitional" means it is not fully calcined.

Preferred transesterification catalysts used in the second aspect include anion-exchange resins having tertiary amine, quaternary ammonium, sulfonic acid or carboxylic acid functional groups; solid inorganic compounds, such as, alumina or pseudoboehmite; solid support catalysts containing alkaline earth metal halides, such as, those described in U.S. Pat. No. 5,498,743, which is incorporated herein by reference; or inorganic solid support catalysts containing ions, metals, compounds or complexes of at least one element of Groups 1, 2, 4-10, 12 and 13-17 (IUPAC classification, previously Groups 1A, 2A, 4B-8B, 2B and 3A-7A) of the Periodic Table.

Particularly, preferred transesterification catalysts are or hydroxides, carbonates or bicarbonates of quaternary ammonium bases.

The transesterification reaction of the second aspect is preferably carried out in a continuous mode utilizing various reactor configurations, such as, fixed or packed-bed reactors, in a single or multiple-reactor configuration, or a reactive distillation column, at from about 50° C. up to about 250° C., preferably between about 75° C. up to about 140° C., and at pressures ranging from about atmospheric pressure up to about 13790 kPa (2000 psi), preferably from about 138 kPa (20 psi) up to about 2069 kPa (300 psi). In the preferred mode of operation, the reactor temperature and pressure are optimized to ensure a relatively high conversion and selectivity to the desired dialkyl carbonate and diol and to optimize the economics of the overall integrated process. Generally, a reactive distillation column will tend to give higher conversions of ethylene carbonate and methanol, while a packed-bed reactor offers flexibility in handling various heterogeneous catalysts.

The first embodiment of the integrated process, which utilizes a circulating homogeneous catalyst, is shown schematically in FIG. 1. Equipment not essential to the understanding of the invention, such as, heat exchangers, pumps, compressors and the like are not shown.

Referring now to FIG. 1, the carbonation reactor 1 is preferably a stirred tank reactor in which the alkylene oxide is reacted with CO2 to form alkylene carbonate. The reactor 1 is charged with alkylene oxide, catalyst and recycled ethylene carbonate via line 2 and with CO2 via line 3. It should be noted that the catalyst is mainly dissolved in the recycled ethylene carbonate, with a temporarily high local concentration of ethylene oxide. In the case of ethylene carbonate, the reaction of ethylene oxide and CO2 is exothermic and the temperature of the reaction zone is usually maintained below about 250° C. and the pressure is maintained in the range from about 500 to about 1000 psia to enhance product quality, yield and selectivity. Preferably, the reaction temperature is between about 150° C. and 200° C. The molar ratio of CO2 to ethylene oxide is generally maintained at about 1.3:1 to 1:1, preferably 1.15:1 to 1.05:1. Preferably, the effluent from reactor 1 is fed to a tubular polishing reactor 4, to obtain greater than 90% overall conversion of the alkylene oxide.

The carbonation reactor effluent is withdrawn from reactor 4 via line 5. The carbonation reactor effluent 5 contains cyclic carbonate, unreacted CO2, a small amount of unreacted alkylene oxide, halogen-free carbonation catalyst, and by-product impurities, such as, mono- and poly-glycols. Also provided on reactor 1 is vent line 6 which can be operated continuously or intermittently to purge the reactor of volatile impurities which could unfavorably affect product quality. For example, in the case of ethylene carbonate synthesis from ethylene oxide and CO2, acetaldehyde is formed which, if it remained in the reaction mixture, could initiate side reactions to form unwanted polymeric materials or other byproducts that could unfavorably affect product quality.

The carbonation reactor effluent is fed from line 5 into separator 7 from which CO2 and unreacted alkylene oxide is separated as a gaseous effluent and, optionally, returned to the carbonation reactor 1 via lines 8 and 3. A purge line 9 is also provided to vent some or all of the overhead gas from separator 7. Separator 7 is preferably a simple flash unit. In the case of ethylene carbonate the reactor effluent is flashed at pressures ranging from about 0.5 up to about 30 psia and temperatures between about 120° C. and 200° C. The liquid effluent will typically contain about 0.1 to 5 wt % catalyst, about 0.3 to 20 wt % polyglycols, about 0.2 to 20 wt % mono-ethylene glycol and about 90 to 99 wt % ethylene carbonate.

The liquid effluent from separator 7 is passed via line 10 into a transesterification reactor 11, which is preferably a tubular reactor or a stirred tank followed by a tubular section. An aliphatic monohydric alcohol is also fed to transesterification reactor 11 via line 12. The molar ratio of alcohol to cyclic carbonate fed to reactor 11 is generally from about 2:1 to about 6:1, preferably about 3:1 to about 4:1. In the case of dimethyl carbonate and ethylene glycol, the reaction of ethylene carbonate and methanol will be maintained at a temperature of about 80° C. to 200° C., preferably about 100° C. to 150° C., and pressures about 690 kPa (100 psi) to 2069 kPa (300 psi). The conversion per pass of ethylene carbonate to dimethyl carbonate is about 30 to 70%, preferably about 50 to 70%, most preferably about 50 to 65%.

The transesterification reactor effluent is withdrawn from reactor 11 via line 13. The transesterification reactor effluent 13 will typically contain dialkyl carbonate, a diol, unreacted cyclic carbonate, unreacted alcohol, homogeneous catalyst and by-products, such as, organic oxygenates and polyglycols. However, the composition, and by-product yields, in particular, can vary widely based upon the specific catalyst and operating conditions employed.

The transesterification reactor effluent is fed from line 13 into a distillation column 14, where an overhead product stream containing the dialkyl carbonate, alcohol and organic oxygenates is removed via line 15 and a bottoms product stream containing the diol, cyclic carbonate, halogen-free carbonation catalyst and polyglycols is removed via line 16. In the case of dimethyl carbonate and ethylene glycol, the distillation column is typically operated at a pressure of between about 5 and 30 psia and a temperature range at the top of the column of about 50° C. to 90° C. Optionally, a side-stream 17 is withdrawn from column 14, which is depleted of the diol and cyclic carbonate, and recycled to transesterification reactor 11 to reduce the load on dialkyl carbonate product distillation column 18.

Figure 5:
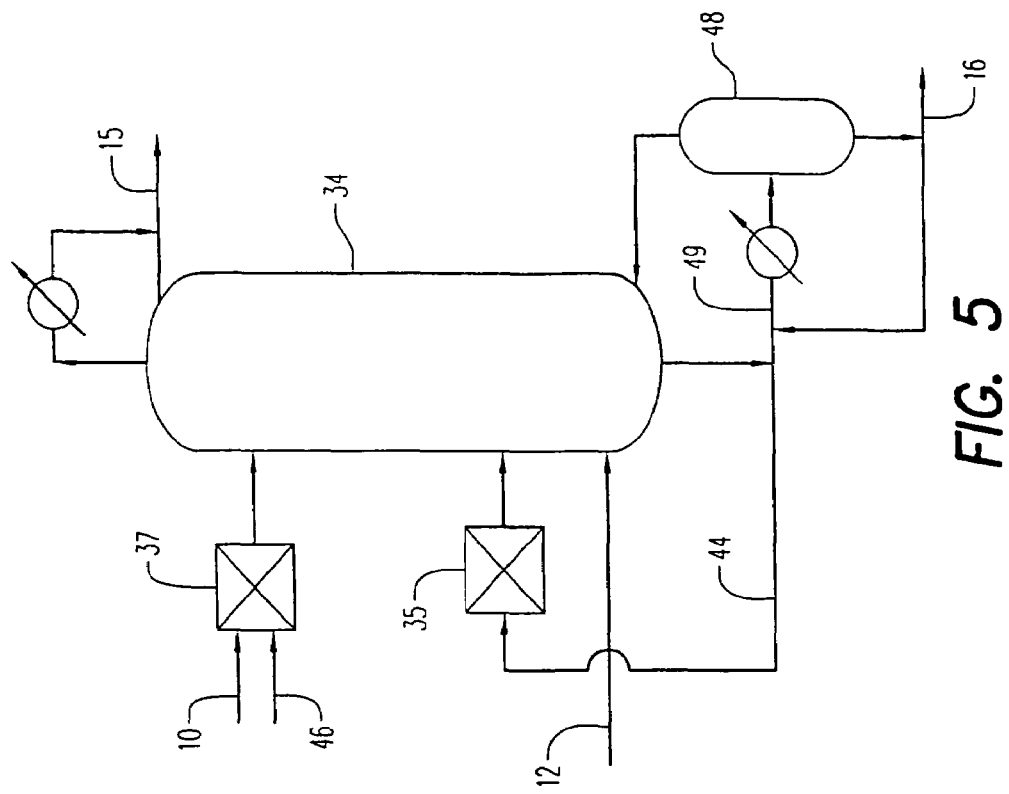
FIG. 5 is a schematic representation of a transesterification distillation tower with upper and lower external reaction zones having a bottoms recycle assembly.
Figure 4:
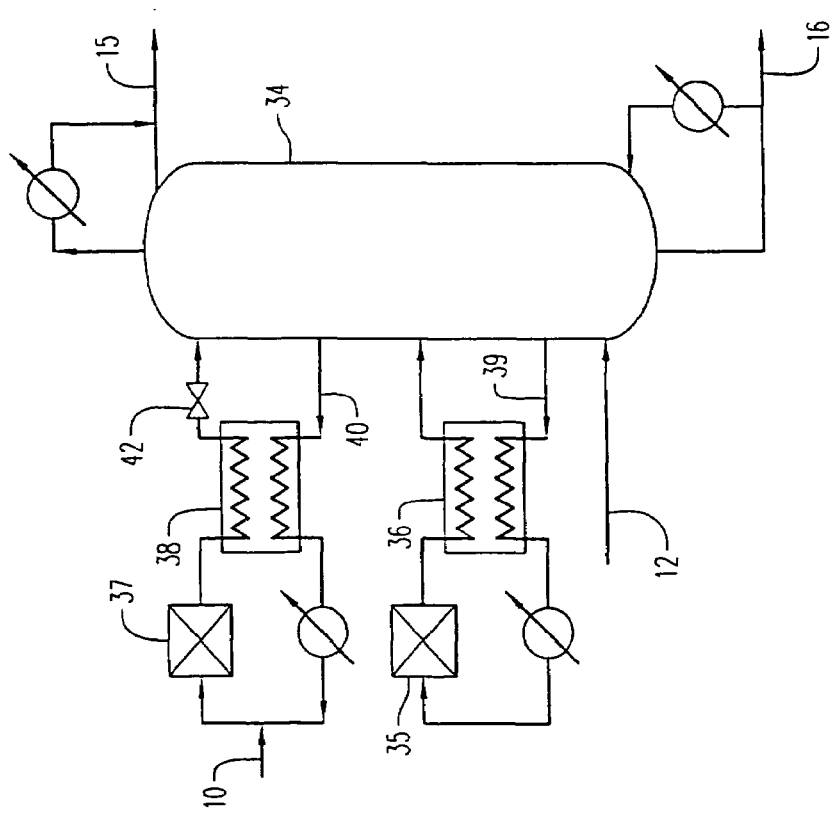
FIG. 4 is a schematic representation of a transesterification distillation tower with upper and lower external reaction zones with integrated heat exchangers at each reaction zone.

Alternatively, as shown in FIGS. 4 and 5, transesterification reactor 11 and distillation column 14 can be replaced with a single distillation tower 34 comprising a plurality of reaction zones 35 and 37 communicating with a plurality of heat exchangers 36 and 38 via conduits 39 and 40, respectively. Such a configuration allows reaction zones 35 and 37 to operate at different temperatures than distillation tower 34. With the addition of a pressure-reducing device 42, reaction zone 37 can also operate at a different pressure.

FIG. 5 depicts another embodiment using distillation tower 34 wherein the bottoms are recycled via conduit 44 and reaction zone 35 to a lower portion of distillation tower 34. The upper reaction zone 37 is a once through process wherein alkylene carbonate (e.g., ethylene carbonate) is fed via conduit 10 and an alkanol (e.g., methanol) is feed via conduit 46. Bottoms can also be transported to knock-out drum 48 via conduit 49, wherein the vapor from knock-out drum 48 is recycled to tower 34 and the bottoms of knock-out drum 48 sent via conduit 16 for subsequent downstream treatment. The configurations shown in FIGS. 4 and 5 can allow greater conversion of alkylene carbonate than would be obtained in a single reactor.

The overhead product stream is fed via line 15 to dialkyl carbonate product distillation column 18, where the alcohol is taken overhead and recycled via lines 19 and 12 to transesterification reactor 11 and dialkyl carbonate product is removed from the bottom of reactor 11 via line 20 and sent to storage. A purge stream 21 is also provided to prevent the accumulation of light by-product impurities. In the case of a dimethyl carbonate, the dialkyl carbonate product distillation column 18 is typically operated at a pressure of about 828 kPa (120 psia) to 1379 kPa (200 psia) and a temperature range for about 120° C. to 190° C. Dimethyl carbonate and methanol form a low-boiling azeotrope, so that the overhead stream includes up to about 15 wt %, and typically about 5-15 wt %, dimethyl carbonate. This dimethyl carbonate is recycled to transesterification reactor 11 along with the methanol via conduits 21, 19 and 12.

The bottoms product stream from distillation column 14 is fed via conduit 16 to diol product distillation column 22, where the diol product is removed overhead via conduit 23 and sent to storage or for further processing, and a bottoms stream containing unreacted cyclic carbonate, halogen-free carbonation catalyst, polyglycols and other heavies is removed via conduit 25. Optionally, the diol product which is taken overhead via conduit 23 may be withdrawn from an intermediate point in column 22, and the overhead product from column 22 is returned to an intermediate feed point in column 14. A hydrolysis reactor can also be incorporated into the integrated process to provide a highly purified diol, e.g., ethylene glycol. The feed to this hydrolysis reactor can include the diol product stream, which may contain small amounts of cyclic carbonate, and some or all of the unreacted cyclic carbonate containing stream, that is otherwise recycled to the transesterification reactor. Water is also fed to the hydrolysis reactor to convert cyclic carbonate to diol with the formation of $CO_2$ by-product. In the case of ethylene glycol, distillation column 22 is operated in a temperature range of about 100° C. to 170° C., under a vacuum in the range of about 50 to 200 mm Hg. A portion of this bottoms stream is recycled to the carbonation reactor 1 via conduits 24 and 2. Purge conduit 25 is provided to prevent accumulation of polyglycols and other heavies. The heavies stream from purge conduit 25 may be subjected to vacuum evaporation or distillation to recover valuable ethylene carbonate. Make-up and recycled halogen-free carbonation catalyst is fed via conduits 26 and 24, respectively, into conduit 2. A portion of the bottoms stream is also recycled to the transesterification reactor 11 via lines 24, 27, and 10. The proportion of the bottoms stream which is recycled to each reactor 1 and 11 will be chosen to optimize the economics of the process and will depend upon the specific dialkyl carbonate and diol being produced.

In another embodiment, at least a portion of the bottoms stream from diol product distillation column 22 can be fed to an evaporator (not shown) from which a cyclic carbonate-rich stream is recovered as a vaporous effluent and recycled to transesterification reactor 11. In the case of ethylene carbonate, the operating conditions of the evaporator typically include temperatures in the range of about 120° C. to 180° C., under a vacuum in the range of about 10 to 80 mm Hg. A liquid effluent stream from the evaporator, rich in catalyst, is also recovered and recycled to carbonation reactor 1.

The second embodiment of the integrated process, which utilizes a circulating carbonation catalyst and a heterogeneous transesterification catalyst, is accomplished as described above with reference to FIG. 1, however the second aspect includes several process condition modifications. The foregoing description of FIG. 1 applies equally to the description of FIG. 2 except that the following process condition modifications are specific to the carbonation catalyst—heterogeneous transesterification catalyst process depicted in FIG. 2.

Figure 2:
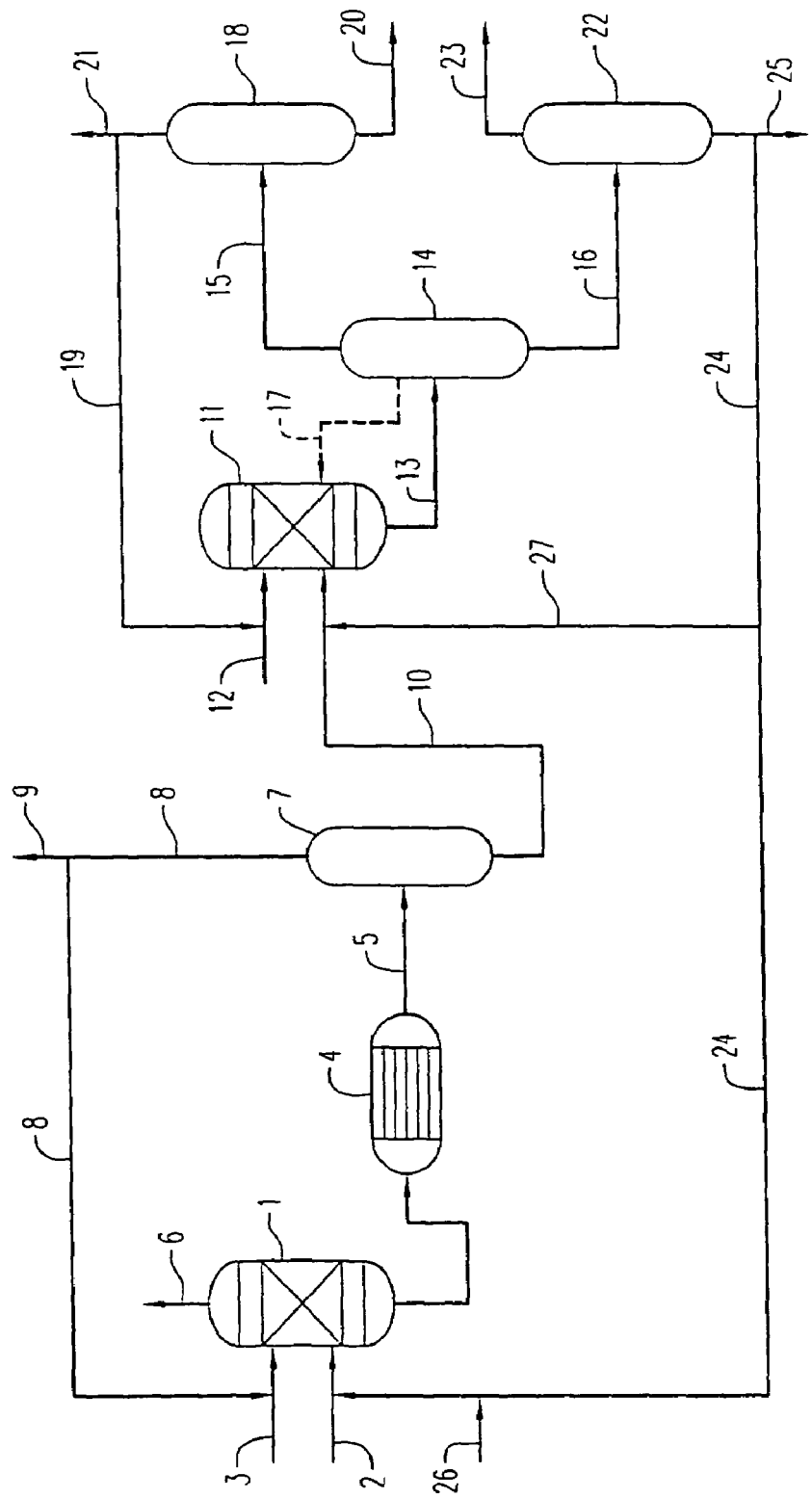
FIG. 2 is a schematic of an embodiment of the integrated process, which utilizes a circulating halogen-free carbonation catalyst and a heterogeneous transesterification catalyst.

Referring now to FIG. 2, as in the first aspect, reactor 1 is charged with alkylene oxide and catalyst via conduit 2 and with $CO_2$ via conduit 3. In the case of ethylene carbonate, the reaction of ethylene oxide and $CO_2$ is exothermic and the temperature of the reaction zone in the second aspect of the invention is usually maintained below about 220° C. and the pressure is maintained in the range from about 3448 kPa (500 psi) to about 6897 kPa (1000 psi) to enhance product quality. Preferably, the reaction temperature is between about 180° C. and 200° C.

In the second aspect, the liquid effluent from separator 7 is passed via conduit 10 into transesterification reactor 11, which is preferably a fixed-bed reactor. The WHSV in the fixed-bed reactor of the second aspect is generally about 0.3 to 3 hr−1.

As in the first aspect, a hydrolysis reactor can also be incorporated into the integrated process of the second aspect to provide a highly purified diol, e.g., ethylene glycol. The feed to this hydrolysis reactor can include the diol product stream, which may contain small amounts of cyclic carbonate, and some or all of the unreacted cyclic carbonate containing stream, that is otherwise recycled to the transesterification reactor. Water is also fed to the hydrolysis reactor to convert cyclic carbonate to diol with the formation of $CO_2$ by-product.

Figure 3:
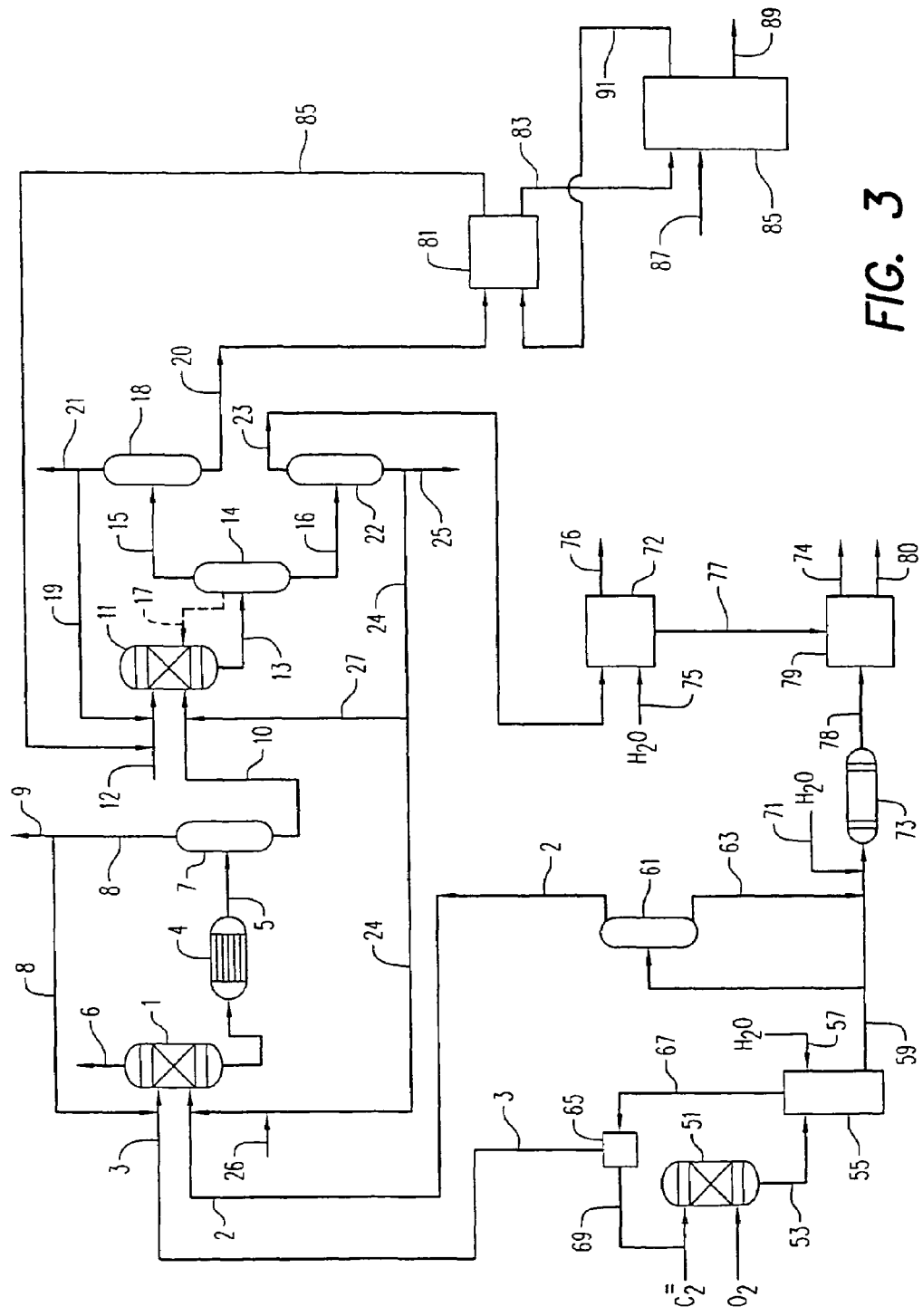
FIG. 3 is a schematic representation of a reaction process for the production of polycarbonate from ethylene utilizing the integrated process according to FIGS. 1 and 2 above.

Use of the integrated process of all aspects of the present invention for the production of dimethyl carbonate and ethylene glycol is particularly well suited for incorporation into an ethylene glycol plant, which produces ethylene glycol from ethylene, oxygen and water by the method described in the Encyclopedia of Chemical Processing and Design, J. J. McKetta, Marcel Dekker, Inc., N.Y., pp. 237 to 243 (1984), which is incorporated herein by reference. Such a process is depicted in FIG. 3, wherein ethylene is first reacted with oxygen in a selective oxidation reactor 51 to produce ethylene oxide, $CO_2$ and water (i.e., a gas mixture) which are removed from reactor 51 via conduit 53. This gas mixture typically includes unconverted ethylene and one or more relatively insert 'ballast' components, such as, methane. The gas mixture containing ethylene oxide is fed via conduit 53 to absorber unit 55 where it is contacted with $H_2O$ fed via conduit 57, to absorb most of the ethylene oxide in the water. The ethylene oxide in water is taken as bottoms from absorber unit 55 via conduit 59 to distillation column 61 wherein ethylene oxide is taken overhead from column 61 via conduit 2 and fed to carbonation reactor 1 as discussed above in FIG. 1, and $H_2O$, ethylene glycol, polyglycols and residual ethylene oxide are removed as bottoms via conduit 63 to join the feed to hydration reactor 73. Additional water 71 may be added to the feed of hydration reactor 73, to adjust the water to ethylene oxide ratio to a preferred range of between about 10:1 to 30:1. Hydration reactor 73 preferably contains no catalyst, and operates at 120° C. to 250° C. and pressure sufficient to keep the components in the liquid phase. Products from hydration reactor 73 are taken via conduit 78 to glycol separations unit 79, which removes water and produces an ethylene glycol product stream 74, and residual polyglycol stream 80. Optionally, the various polyglycols, such as, ethylene glycol and triethylene glycol, may be produced as separate product streams.

The diol product stream from column 22, which may contain up to about 20% by weight ethylene carbonate, is taken via conduit 23 to hydrolysis unit 72. $H_2O$ is added to this unit, and most of the ethylene carbonate entering the unit is hydrolyzed to ethylene glycol, which is removed via conduit 77, and to $CO_2$, which is removed via conduit 76. This $CO_2$ may, optionally, be recycled to carbonation reactor 1.

The overhead from absorber unit 55 which includes ethylene, $CO_2$ and ballast gas is fed to $CO_2$ separation unit 65 via conduit 67 wherein CO2 is taken overhead from CO2 separation unit 65 via conduit 71 wherein it is either released to the atmosphere or fed to carbonation reactor 1 via conduit 3, and residual gas taken via conduit 69 is recycled to selective oxidation reactor 51.

The removed ethylene oxide can be returned as ethylene glycol, essentially on a 1:1 mole basis. Moreover, since the ethylene glycol produced in accordance with the present invention is primarily mono-ethylene glycol, the amount of ethylene oxide that becomes mono-ethylene glycol as opposed to polyethylene glycols can be actually greater via the integrated process than by the ethylene glycol plant. As such, the ethylene glycol, having a higher percentage of mono-ethylene glycol, can be returned to the ethylene glycol plant just prior to the purification equipment, reducing the amount of glycol purification required for the volume returned. This is especially beneficial for the production of fibergrade mono-ethylene glycol, which has a minimum purity specification of 99.9 wt % mono-ethylene glycol.

Substantially pure dialkyl carbonate (e.g., dimethyl carbonate) is taken as bottoms via conduit 20 from distillation column 18 and fed, for example, into diphenyl carbonate production unit 81 having at least one reactor with metal-containing catalyst operating at 80° C.-300° C. and 2-4,000 kPa, and having associated separation devices. This diphenyl carbonate production unit 81 produces diphenyl carbonate and methanol. The methanol is taken overhead via conduit 85 and recycled via conduit 12 to transesterification reactor 11. The diphenyl carbonate is removed from diphenyl carbonate production unit 81 as bottoms stream via conduit 83. The diphenyl carbonate is thereafter reacted within polycarbonate reactor 85 with bisphenol-A, thereby producing polycarbonate and phenol. The polycarbonate is removed as a sidestream via conduit 89 and sent to storage, and the phenol is taken overhead via conduit 91 and recycled to diphenyl carbonate production unit 81.

It is contemplated that the unique integrated process for producing dialkyl carbonate from alkylene and an oxygen-containing gas can be used cost effectively to produce commercial quantities of other products, such as, furazolidone, agrochemical/pharmaceutical intermediates, allyl diglycol carbonate (e.g., eye glass lenses), linear alkylcarbonate lubricants, oligocarbonate, light emitting diodes for outdoor display panels and gasoline octane improver.

EXAMPLE 1

Set forth below are data from two commercial processes for the manufacture of dimethyl carbonate, as well as a sample of the crude dimethyl carbonate product produced by the unique low corrosive integrated process according to the present invention. Sample 1 below was generated from a standard process which employs a chloride copper catalyst, as well as a continuous HCl injection or mitigation step to maintain catalyst activity. Sample 2 was also generated from a standard process which employs a chloride copper catalyst, as well as a continuous HCl injection or mitigation step to maintain catalyst activity.

The analytical results are set forth below in Table 1:

TABLE 1

|  | SAMPLE 1 | SAMPLE 2 |
|---|---|---|
| GC Purity | 99.83 | 100 |
| TAN | 0.0427 mg/g KOH | 0.0996 mg/g KOH |
| KF Water | 113 ppm | 79.4 ppm |
| % Cl (XRF) | 12 ppm | 7 ppm |
| Metals (ICP) | Cd = 0.0068 ppm | Cr = 0.0088 ppm |
|  | Co = 0.0060 ppm | Fe = 0.0481 ppm |
|  | Cu = 0.0091 ppm | K = 0.35 ppm |
|  | Fe = 0.0767 ppm | Mo = 0.020 ppm |
|  | K = 0.98 ppm | Ni = 0.018 ppm |
|  | Mg = 0.040 ppm |  |
|  | Mn = 0.0046 ppm |  |
|  | Na = 0.378 |  |
|  | Zn = 0.0084 ppm |  |
| Appearance | Water-white | Water-white |

As set forth above in Table 1, Samples 1 and 2 exhibit greater than 5 ppm of Cl which is extremely undesirable and corrosive to the dimethyl carbonate. The higher the level of chlorine, the greater risk of corrosion, i.e., dimethyl carbonate reacting on the reaction vessels and conduits such that there is a substantial increase of metal content in the crude dimethyl carbonate product.

What is claimed is:

1. An integrated process for the production of a dialkyl carbonate and a diol from an alkylene oxide, carbon dioxide and an aliphatic monohydric alcohol comprising:

(a) reacting an alkylene oxide with carbon dioxide in the presence of a chlorine-free carbonation catalyst, wherein the carbonation catalyst is selected from the group consisting of [1,1'(1-butylbenzimidazol-2yl)pentane]copper(II) di(trifluoromethanesulfonate) and hydroxides of quaternary ammonium bases at a temperature in the range of about 50° C. to 250° C. and at a pressure of at least about 1379 kPa (200 psi) to provide a crude cyclic carbonate stream comprising a cyclic carbonate and said catalyst; and (b) reacting said cyclic carbonate with said aliphatic monohydric alcohol in the presence of said catalyst to provide a crude product stream comprising said dialkyl carbonate and said diol, wherein said crude product stream exhibits a chloride concentration of about 5 ppm or less.

* * * * *